United States Patent [19]

Langbein et al.

[11] 4,069,328
[45] Jan. 17, 1978

[54] PHARMACEUTICAL COMPOSITIONS CONTAINING AN N-(FURYL-METHYL)-2'-HYDROXY-5,9,9-TRIMETHYL BENZOMORPHAN AND METHOD OF USE

[75] Inventors: Adolf Langbein; Herbert Merz; Gerhard Walther; Klaus Stockhaus, all of Ingelheim am Rhein, Germany

[73] Assignee: Boehringer Ingelheim GmbH, Ingelheim am Rhein, Germany

[21] Appl. No.: 732,708

[22] Filed: Oct. 15, 1976

Related U.S. Application Data

[60] Division of Ser. No. 599,427, July 28, 1975, Pat. No. 4,010,164, which is a continuation-in-part of Ser. No. 454,964, March 27, 1974, abandoned.

[30] Foreign Application Priority Data

Mar. 28, 1973 Germany .............................. 2315339

[51] Int. Cl.² ................. A61K 31/445; A61K 31/455
[52] U.S. Cl. ..................................... 424/266; 424/267
[58] Field of Search .............................. 424/266, 267

Primary Examiner—Stanley J. Friedman
Attorney, Agent, or Firm—Hammond & Littell

[57] ABSTRACT

Pharmaceutical compositions containing as an active ingredient compounds of the formula

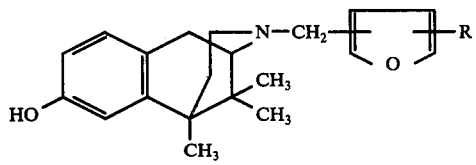

wherein R is hydrogen or methyl, or a non-toxic, pharmacologically acceptable acid addition salt thereof; and a method of using the same as morphine-antagonists and analgesics.

12 Claims, No Drawings

PHARMACEUTICAL COMPOSITIONS CONTAINING AN N-(FURYL-METHYL)-2'-HYDROXY-5,9,9-TRIMETHYL BENZOMORPHAN AND METHOD OF USE

This is a division of copending application Ser. No. 599,427 filed July 28, 1975, now U.S. Pat. No. 4,010,164 granted March 1, 1977; which in turn is a continuation-in-part of application Ser. No. 454,964 filed Mar. 27, 1974, now abandoned.

This invention relates to novel pharmaceutical compositions containing an N-(furyl-methyl)-2'-hydroxy-5,9,9-trimethyl-benzomorphan or a non-toxic acid addition salt thereof, as well as to a method of using these compounds as morphine-antagonists and analgesics.

More particularly, the present invention relates to novel pharmaceutical compositions comprising as an active ingredient an N-(furyl-methyl)-2'-hydroxy-5,9,9-trimethyl-benzomorphan represented by the formula

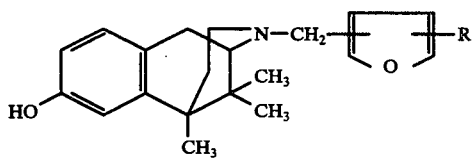

(I)

wherein R is hydrogen or methyl, or a non-toxic, pharmacologically acceptable acid addition salt thereof.

These compounds occur as optically inactive racemates or racemic mixtures, as well as optical antipodes, and the present invention includes compositions comprising the optically inactive or the optically active forms of these compounds.

The benzomorphan derivatives embraced by formula I may be prepared by the following methods:

METHOD A

By reacting 2'-hydroxy-5,9,9-trimethyl-norbenzomorphan of the formula

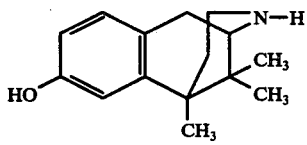

(II)

with a furylmethyl derivative of the formula

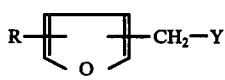

(III)

wherein
R has the same meanings as in formula I, and
Y is halogen, preferably chlorine or bromine, alkylsulfonyloxy or arylsulfonyloxy.

The reaction is advantageously performed in the presence of an acid-binding agent and of an inert solvent medium, by providing the calculated amount of the alkylating agent of the formula III or a slight excess thereover. Examples of suitable acid-binding agents are tertiary amines, such as triethylamine or N,N-dicyclohexyl-ethylamine; alkali metal carbonates, such as sodium carbonate or potassium carbonate; alkali metal bicarbonates, preferably sodium bicarbonate; alkali metal hydroxides; or alkali metal oxides. Examples of suitable inert solvent media are tetrahydrofuran, dioxane, methylene chloride, dimethylformamide, dimethylsulfoxide or mixtures of any two or more of these, preferred are mixtures of tetrahydrofuran an dimethylformamide. The reaction temperature is variable within wide limits, but the preferred reaction temperature range is from 0° C to the boiling point of the particular solvent medium which is used.

After completion of the reaction, the desired end product is isolated, purified and crystallized by conventional methods.

METHOD B

By reducing a 2'-oxy-5,9,9-trimethyl norbenzomorphan amide of the formula

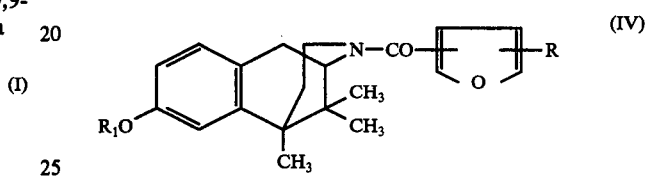

(IV)

wherein
R has the same meanings as in formula I, and
$R_1$ is hydrogen or acyl,
with a complex metal hydride, preferably lithium aluminum hydride.

The reduction is effected by using the calculated amount or advantageously an excess, preferably twice the calculated amount, of the complex metal hydride. The reaction is carried out in the presence of an inert solvent medium, such as an ether, preferably tetrahydrofuran. The reaction temperature may be varied within wide limits, but the preferred temperature range is, as in method A, between 0° C and the boiling point of the solvent medium.

When the complex metal hydride reduction is applied to an O-acyl-benzomorphanamide, i.e. a compound of the formula IV wherein $R_1$ is acyl, especially lower alkanoyl, the acyl substituent is split off simultaneously with the reduction of the carbonyl group, resulting in the formation of a compound of the formula I.

The desired end product may be isolated, purified and crystallized by conventional methods.

The starting compound of the formula II for method A is described in German Offenlegungsschrift No. 2,027,077.

The compounds of the formula III wherein Y is halogen may be prepared by reducing a corresponding known furancarboxylic acid ester to form a hydroxymethyl-furan, which may subsequently be converted into the corresponding halomethyl-furan with the aid of an acid halide by conventional procedures. Compounds of the formula III wherein Y is alkylsulfonyloxy or arylsulfonyloxy may be prepared analogously by esterifying a corresponding hydroxy-methyl-furan with the desired sulfonic acid.

The starting compounds of the formula IV may be prepared by reacting the norbenzomorphan of the formula II with a furan-carboxylic acid chloride of the formula

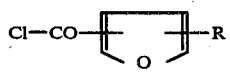

(V)

wherein R has the meanings previously defined.

A compound of the formula V, in turn, may be obtained by reacting a corresponding furan-carboxylic acid with an inorganic acid chloride, such as phosphorus pentachloride, phosphorus oxychloride or thionyl chloride.

The compounds embraced by formula I are organic bases and therefore form acid addition salts with inorganic or organic acids. Examples of non-toxic, pharmacologically acceptable acid addition salts are those formed with hydrochloric acid, hydrobromic acid, hydroiodic acid, acetic acid, propionic acid, butyric acid, valeric acid, hydrofluoric acid, sulfuric acid, phosphoric acid, nitric acid, pivalic acid, caproic acid, capric acid, oxalic acid, malonic acid, succinic acid, maleic acid, fumaric acid, lactic acid, tartaric acid, citric acid, benzoic acid, p-hydroxy-benzoic acid, phthalic acid, cinnamic acid, salicyclic acid, ascorbic acid, 8-chlorotheophylline, methanesulfonic acid or the like. Such acid addition salts are obtained in conventional manner, i.e. by dissolving the free base in an alcohol or ketone, and adding an ethereal solution of the desired acid.

The following examples illustrate the preparation of compounds of the formula I and non-toxic acid addition salts thereof.

EXAMPLE 1

N-Furfuryl-2'-hydroxy-5,9,9-trimethyl-6,7-benzomorphan and its hydrochloride by method B 2.31 gm (0.01 mol) of 2'-hydroxy-5,9,9-trimethylbenzomorphan were dissolved in 30 ml of absolute methylene chloride, 4 ml of triethylamine were added to the solution, and then 1.44 gm (0.011 mol) of 2-furan-carboxylic acid chloride were added dropwise over a period of 15 minutes at room temperature. The reaction mixture was then refluxed for one hour, subsequently diluted with methylene chloride, and then repeatedly vigorously shaken with water. The organic phase was dried with sodium sulfate, evaporated, the residue was dissolved in 35 ml of absolute tetrahydrofuran, and the resulting solution was added dropwise at room temperature to a solution of 0.76 gm (0.02 mol) of lithium aluminum hydride in 35 ml of absolute tetrahydrofuran. The reaction mixture was then refluxed for two hours, allowed to cool, and subsequently carefully admixed with 76 ml of an aqueous saturated solution of diammonium tartrate. The resulting mixture was allowed to stand at room temperature for a long period of time, whereupon the aqueous phase was separated from the tetrahydrofuran phase. The aqueous phase was extracted twice with 100 ml of methylene chloride each, and the extracts were combined and added to the tetrahydrofuran phase. The combined organic solutions were vigorously washed with water, dried over sodium sulfate and evaporated. The oily residue, the free base N-furfuryl-2'-hydroxy-5,9,9-trimethyl-6,7-benzomorphan, was dissolved in 20 ml of absolute ethanol, and the resulting solution was admixed with 5 ml of 2 N ethereal hydrochloric acid. Upon careful addition of ether to the acidic solution, a crystalline precipitate was formed which was collected by filtration, yielding 2.8 gm (80.6% of theory) of the hydrochloride of the formula

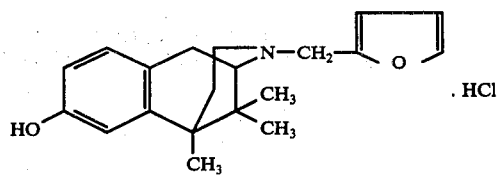

which had a melting point of 180°–184° C.

EXAMPLE 2

Using a procedure analogous to that described in Example 1, 69% of theory of N-(3-furyl-methyl)-2'-hydroxy-5,9,9-trimethyl-6,7-benzomorphan hydrochloride, m.p. 255-258° C, was obtained from 2'-hydroxy-5,9,9-trimethyl-benzomorphan and 3-furan carboxylic acid chloride.

EXAMPLE 3

Using a procedure analogous to that described in Example 1, 83.2% of theory of N-(2-methyl-3-furylmethyl)-2'-hydroxy-5,9,9-trimethyl-6,7-benzomorphan methanesulfonate, m.p. 214°–216° C, was obtained from 2'-hydroxy-5,9,9-trimethylbenzomorphan, 2-methyl-3-furan-carboxylic acid chloride and methanesulfonic acid.

EXAMPLE 4

Using a procedure analogous to that described in Example 1, 55.4% of theory of N-(3-methyl-furfuryl)-2'-hydroxy-5,9,9-trimethyl-6,7-benzomorphan hydrochloride, m.p. 201°–204° C, was obtained from 2'-hydroxy-5,9,9-trimethyl-benzomorphan and 3-methyl-2-furan-carboxylic acid chloride.

The optically inactive as well as optically active forms of compounds embraced by formula I above their nontoxic, pharmacologically acceptable acid addition salts, have useful morphine-antagonistic and analgesic properties. More particularly, those compounds of formula I wherein R is hydrogen exhibit predominantly morphine-antagonistic activities, while those where R is methyl exhibit predominantly analgesic activities in warm-blooded animals, such as mice and rats.

The morphine-antagonistic properties were ascertained by means of the Haffner test [Deutsche Medizinische Wochenschrift 55, 731 (1929)], and the analgesic properties were ascertained by means of the hot-plate test [J. Pharmocal. Exp. Therap. 80, 300 (1944)]and the writhing test [Ibid. 154, 319 (1966)].

For pharmaceutical purposes the compounds of the formula I or their non-toxic addition salts are administered to warm-blooded amimals perorally, parenterally ro rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds of the formula I or their nontoxic acid addition salts is from 0.16 to 5.0 mgm/kg body weight, preferably from 0.83 to 2.5 mgm/kg body weight.

The following examples illustrate a few pharmaceutical dosage unit compositions comprising a compound of the formula I or a non-toxic acid addition salt as an active ingredient and represent the best modes contemplated of putting the invention into practical use. The parts are parts by weight unless otherwise specified.

EXAMPLE 5

Tablets

The tablet composition is compounded from the following ingredients:

| | | |
|---|---:|---|
| N-Furfuryl-2'-hydroxy-5,9,9-trimethyl-6,7-benzomorphan hydrochloride | 50.0 | parts |
| Lactose | 95.0 | " |
| Corn starch | 45.0 | " |
| Colloidal silicic acid | 2.0 | " |
| Soluble starch | 5.0 | " |
| Magnesium stearate | 3.0 | " |
| Total | 200.0 | parts |

Preparation

The benzomorphan compound is intimately admixed with the lactose and the corn starch, the mixture is moistened with an aqueous 10% solution of the soluble starch, the moist mass is forced through a 1 mm-mesh screen, the resulting granulate is dried at 40° C, the dry granulate is admixed with the colloidal silicic acid, and the composition is compressed into 200 mgm-tablets in a conventional tablet making machine. Each tablet contains 50 mgm of the benzomorphan compound and is an oral dosage unit composition with predominantly analgesic action.

EXAMPLE 6

Coated pills

The pill core composition is compounded from the following ingredients:

| | | |
|---|---:|---|
| N-(3-Furylmethyl)-2'-hydroxy-5,9,9-trimethyl-6,7-benzomorphan hydrochloride | 75.0 | parts |
| Lactose | 100.0 | " |
| Corn starch | 65.0 | " |
| Colloidal silicic acid | 2.0 | " |
| Soluble starch | 5.0 | " |
| Magnesium stearate | 3.0 | " |
| Total | 250.0 | parts |

Preparation

The ingredients are compounded in the same manner as in Example 5, and the composition is compressed into 250 mgm-pill cores which are subsequently coated with a thin shell consisting essentially of a mixture of sugar, talcum and gum arabic and finally polished with beeswax. Each coated pill contains 75 mgm of the benzomorphan compound and is an oral dosage unit composition with predominantly analgesic action.

EXAMPLE 7

Suppositories

The suppository composition is compounded from the following ingredients:

| | | |
|---|---:|---|
| N-Furfuryl-2'-hydroxy-5,9,9-trimethyl-6,7-benzomorphan hydrochloride | 50.0 | parts |
| Lactose | 250.0 | " |
| Suppository base (e.g. cocoa butter) | 1400.0 | " |
| Total | 1700.0 | parts |

Preparation

The benzomorphan compound is intimately admixed with the lactose, and the mixture is blended with the aid of an immersion homogenizer into the suppository base which had previously been melted and cooled to about 40° C. 1700 mgmportions of the composition are poured into cooled suppository molds and allowed to harden therein. Each suppository contains 50 mgm of the benzomorphan compound and is a rectal dosage unit composition with predominantly analgesic action.

EXAMPLE 8

Hypodermic solution

The solution is compounded from the following ingredients:

| | | |
|---|---|---:|---|
| N-(2-Methyl-3-furylmethyl)-2'-hydroxy-5,9,9-trimethyl-6,7-benzomorphan hydrochloride | | 50.0 | parts |
| Sodium chloride | | 5.0 | " |
| Double-distilled water | q.s.ad | 5000.0 | " |
| | | | by vol. |

Preparation

The benzomorphan compound and the sodium chloride are dissolved in the double-distilled water, the solution is filtered until free from suspended particles, and the filtrate is filled under aseptic conditions into 2 cc-ampules which are subsequently sterilized and sealed. Each ampule contains 50 mgm of the benzomorphan compound, and its contents are an injectable dosage unit composition with predominantly morphine-antagonistic action.

Analogous results are obtained when one of the other furylmethyl-substituted benzomorphans embraced by formula I or a non-toxic, pharmacologically acceptable acid addition salt is substituted for the particular benzomorphan salt in Examples 5 through 7; or when one of the other methylfurylmethyl-substituted benzomorphans embraced by formula I or a non-toxic, pharmacologically acceptable acid addition salt is substituted for the particular benzomorphan salt in Example 8. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An analgesic pharmaceutical dosage unit composition consisting essentially of an inert pharmaceutical carrier and an effective analgesic amount of a compound of the formula

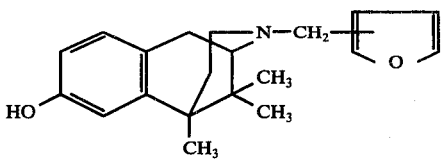

or a non-toxic, pharmacologically acceptable acid addition salt thereof.

2. A composition of claim 1, wherein said compound is N-2'-hydroxy-5,9,9-trimethyl-6,7-benzomorphan or a nontoxic, pharmacologically acceptable acid addition salt thereof.

3. A composition of claim 1, wherein said compound is N-(3-furylmethyl)-2'-hydroxy-5,9,9-trimethyl-6,7-benzomorphan or a non-toxic, pharmacologically acceptable acid addition salt thereof.

4. A morphine-antagonistic pharmaceutical dosage unit composition consisting essentially of an inert pharmaceutical carrier and an effective morphine-antagonistic amount of a compound of the formula

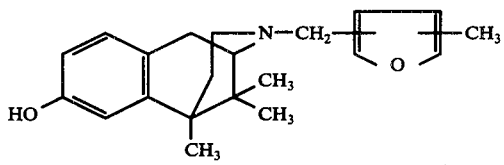

or a non-toxic, pharmacologically acceptable acid addition salt thereof.

5. A composition of claim 4, wherein said compound is N-(2-methyl-3-furylmethyl)-2'-hydroxy-5,9,9-trimethyl-6,7-benzomorphan or a non-toxic, pharmacologically acceptable acid addition salt thereof.

6. A composition of claim 4, wherein said compound is N-(3-methylfurfuryl)-2'-hydroxy-5,9,9-trimethyl-6,7-benzomorphan or a non-toxic, pharmacologically acceptable acid addition salt thereof.

7. The method of relieving pain in a warm-blooded animal, which comprises perorally, parenterally or rectally administering to said animal an effective analgesic amount of a compound of the formula

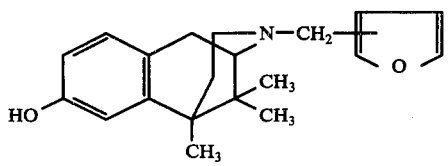

or a non-toxic, pharmacologically acceptable acid addition salt thereof.

8. The method of claim 7 where said compound is N-furfuryl-2'-hydroxy-5,9,9-trimethyl-6,7-benzomorphan or a non-toxic, pharmacologically acceptable acid addition salt thereof.

9. The method of claim 7 where said compound is N-(3-furylmethyl)-2'-hydroxy-5,9,9-trimethyl-6,7-benzomorphan or a non-toxic, pharmacologically acceptable acid addition salt thereof.

10. The method of antagonizing the pharmacological effects of morphine in a warm-blooded animal, which comprises perorally, parenterally or rectally administering to said animal an effective morphine-antagonistic amount of a compound of the formula

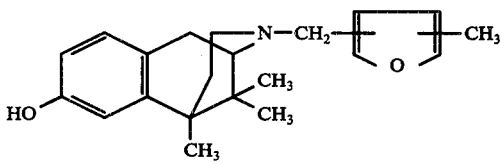

or a non-toxic, pharmacologically acceptable acid addition salt thereof.

11. The method of claim 10, where said compound is N-(2-methyl-3-furylmethyl)-2'-hydroxy-5,9,9-trimethyl-6,7-benzomorphan or a non-toxic, pharmacologically acceptable acid addition salt thereof.

12. The method of claim 10, where said compound is N-(3-methylfurfuryl)-2'-hydroxy-5,9,9-trimethyl-6,7-benzomorphan or a non-toxic, pharmacologically acceptable acid addition salt thereof.

* * * * *